United States Patent [19]
Campbell et al.

[11] Patent Number: 4,580,816
[45] Date of Patent: Apr. 8, 1986

[54] QUICK DISCONNECT TUBE COUPLING

[75] Inventors: Randolph E. Campbell, Red Bank, N.J.; I. Martin Spier, New York, N.Y.

[73] Assignee: E. R. Squibb & Sons, Inc., Princeton, N.J.

[21] Appl. No.: 712,469

[22] Filed: Mar. 15, 1985

Related U.S. Application Data

[63] Continuation of Ser. No. 573,545, Jan. 25, 1984, abandoned.

[51] Int. Cl.⁴ .................................... F16L 21/02
[52] U.S. Cl. .................................. 285/321; 285/347; 285/351; 285/DIG. 22
[58] Field of Search ............ 285/321, DIG. 22, 291, 285/345, 347, 230, 231, 288, 351, 174; 277/1

[56] References Cited

U.S. PATENT DOCUMENTS

| | | | |
|---|---|---|---|
| 216,736 | 6/1879 | Hall | 285/239 |
| 1,979,470 | 11/1934 | Johnston | 285/291 X |
| 2,735,505 | 2/1956 | Kleiman | 285/321 X |
| 2,770,476 | 11/1956 | Cleverly | 285/291 X |
| 2,812,958 | 11/1957 | Rogers | 285/321 X |
| 3,108,755 | 10/1963 | Yartz et al. | 285/DIG. 22 X |
| 3,245,703 | 4/1966 | Manly . | |
| 3,394,954 | 7/1968 | Serms . | |
| 3,533,649 | 10/1970 | Williams | 285/351 X |
| 3,602,009 | 8/1971 | Powell . | |
| 3,603,621 | 9/1971 | Parsons . | |
| 3,637,239 | 1/1972 | Daniel | 285/321 X |
| 3,667,785 | 6/1972 | Kapeker | 285/DIG. 22 X |
| 3,950,483 | 4/1976 | Spier . | |
| 4,111,464 | 9/1978 | Asano et al. | 285/321 X |
| 4,123,091 | 10/1978 | Cosentino et al. . | |
| 4,278,276 | 7/1981 | Ekman | 285/321 X |

FOREIGN PATENT DOCUMENTS

| | | | |
|---|---|---|---|
| 1907474 | 3/1979 | Fed. Rep. of Germany | 285/321 |
| 970583 | 1/1951 | France | 285/239 |
| 29614 | of 1904 | United Kingdom | 285/239 |
| 543733 | 3/1942 | United Kingdom | 285/321 |
| 583459 | 12/1946 | United Kingdom | 285/345 |
| 2092690 | 8/1982 | United Kingdom . | |

Primary Examiner—Thomas F. Callaghan
Attorney, Agent, or Firm—Lawrence S. Levinson; Robert E. Lee, Jr.

[57] ABSTRACT

A tube coupling having a male body, a female body for receiving at least a portion of the male body and at least one peripheral member made from a relatively compressible plastic material molded into a groove within either the relatively rigid male or female body. The peripheral member is disposed to become compresed against a surface of the mating body to form a liquid seal. At least two peripheral members disposed in grooves in a tubular shaped end portion of the male body are made of a compressible plastic and serve as liquid sealing and locking means. The female body comprises a receiving end portion with a tapered interior adapted to receive the male tubular end portion. As the tubular end portion is inserted into the receiving end portion, one of the peripheral members engages the tapered interior surface and becomes compressed there against as the tubular end portion is further inserted. As the tubular end portion is fully inserted a second peripheral member seats itself in a groove in the interior surface of the receiving end portion acting to lock the male and female bodies together. The relatively compressible peripheral members are formed in grooves in the relatively rigid male or female body by insert molding or by simultaneous injection molding of two dissimilar plastics.

5 Claims, 3 Drawing Figures

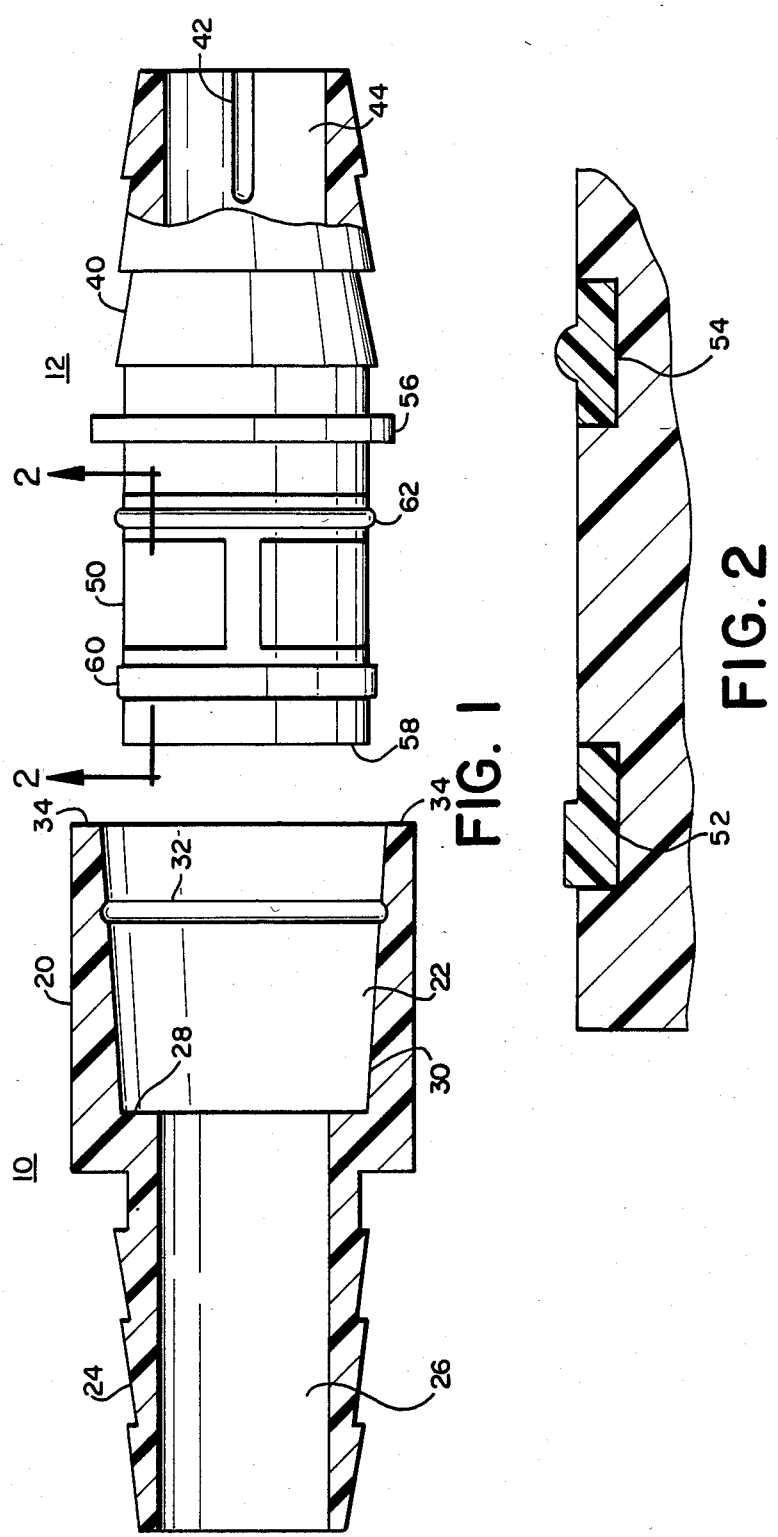

QUICK DISCONNECT TUBE COUPLING

This is a continuation of application Ser. No. 573,545 filed on Jan. 25, 1984, abandoned.

BACKGROUND OF THE INVENTION

This invention relates to an improved tube coupling for connecting the two tube lengths which coupling provides a locking engagement, an effective liquid seal when the tube lengths are connected and a quick disconnect capability. More particularly, the invention relates to tube couplings for medical use although it is not limited to medical applications.

In the prior art many tube couplings are shown comprising a male body and a female body and which provide for a positive locking capability when joining the male and female bodies together. For example, see fingers 34, latch blades 36 and groove 38 in U.S. Pat. No. 3,245,703; see arms 32 and 34 with latch projection 36 and annular shoulder 30 in U.S. Pat. No. 3,394,954; see molded plastic latch 154 in FIG. 2 of U.S. Pat. No. 3,602,009; see the coupling element of FIG. 5 and the rear edge of collar 15 in U.S. Pat. No. 3,603,621; see the inwardly projecting flanges 18 and recessed collar member 21 in U.S. Pat. No. 4,123,091; and the intermediate ring 100 and rim 58 of published UK Patent Application No. GB 2,092,690 A. The various locking mechanisms described in the above-mentioned patent applications are released so that the couplings can be disconnected by either applying a squeezing type pressure to a portion of the latch or locking mechanism (U.S. Pat. Nos. 3,245,703; 3,394,954; 3,602,009; and the UK Patent Application), or by turning, twisting or rotating various portions of the couplers relative to one another (U.S. Pat. Nos. 3,603,621 and 4,123,091).

To provide a liquid seal various approaches are used in the prior art, but one of the most common comprises placement of separately manufactured O-rings in annular grooves surrounding a portion of the male body which portion is inserted in a corresponding cavity of the female body. In particular, see the pair of O-rings 13 and 28 in U.S. Pat. Nos. 4,123,091 and 3,394,954, respectively. O-rings generally function by having a larger outer diameter when placed in the grooves on the male member than the outer diameter of the corresponding portion of the male member. The O-rings are made of a compressible material such as rubber and when inserted in the female cavity, they are compressed against the relatively smooth interior surface thereof to form a liquid seal.

As described above the various prior art devices require separate approaches for providing a locking mechanism and a liquid seal. Further, the prior art devices require some form of separate action to remove the locking action of the locking device; and require the inclusion of separately manufactured O-rings in the assembly of the tube coupling.

SUMMARY OF THE INVENTION

An object of the present invention is to provide an improved tube coupling device.

A further object of the present invention is to provide a simplified tube coupling with a quick disconnect capability.

Still a further object is to provide the above mentioned tube coupling which tube coupling provides an effective liquid seal.

Another object of the present invention is to provide the above mentioned tube coupling having a positive locking action.

Another object of the present invention is to provide the above mentioned tube coupling wherein the means for providing a liquid seal and locking action is integral with either the male or female portion of the coupling.

A further object of the present invention is to provide the above mentioned tube coupling wherein the means for sealing and locking does not interfere in the quick disconnect capability of the tube coupling.

The present invention tube coupling comprises a male body and a female body. At least one peripheral member made from a relatively compressible plastic material is disposed within a groove of one of the bodies. The peripheral member becomes compressed against the surface of the remaining one of the bodies when the male and female bodies are matingly engaged. In a preferred embodiment, the at least one peripheral member is molded within a groove surrounding a hollow plug end portion of the male body. Where the male body is further made of a synthetic plastic material formed in a mold it further comprises an alignment means for properly aligning the male body after forming thereof to accept forming of the peripheral member in the groove by subsequent insert molding.

The present invention tube coupling further comprises a male body, a female body and a locking and a liquid sealing means. The locking and sealing means comprises at least a pair of spaced apart peripheral members which are disposed within grooves in one of the bodies, a first one of the peripheral members disposed to be compressed against the surface of the remaining body to form a liquid seal therewith. The second one of the peripheral members fits within a groove located within the mating body when the male and female bodies are matingly engaged.

In one embodiment of the invention, a pair of spaced apart peripheral members are disposed within grooves surrounding a hollow plug end portion of the male body. One of the peripheral members is disposed to be compressed against the interior surface of a receiving end portion of the female body to provide a liquid seal while the other peripheral member is disposed to fit within a groove located within the interior surface of the receiving end portion of the female body. Alternatively, the peripheral members could be disposed within the interior surface of the receiving end portion and an annular groove for receiving one of the peripheral members surrounds the plug end portion of the male body.

In the preferred embodiment of the present invention, the peripheral member which provides the primary liquid seal with the interior surface of the mating body has a substantially rectangular cross section, while the peripheral member providing a substantial locking action has a circular cross section.

In one embodiment of the present invention, the receiving end portion of the female body is tapered.

Preferably, the locking and sealing means are made of a an elastomeric thermoplastic resin material and is integrally formed with either the male or female body made from a high density polyethylene or polypropylene.

Other features and advantages of the invention will become apparent from the following description read in conjunction with the attached drawings in which:

BRIEF DESCRIPTION OF THE DRAWINGS

FIG. 1 is a longitudinal view of the male and female bodies of the present invention, the female body being shown in cross section and the male body being shown partially in cross section.

FIG. 2 is an enlarged cross-sectional view of a portion of the male body of FIG. 1 taken along the lines and arrows 2.

DETAILED DESCRIPTION OF THE DRAWINGS

Figure 3:
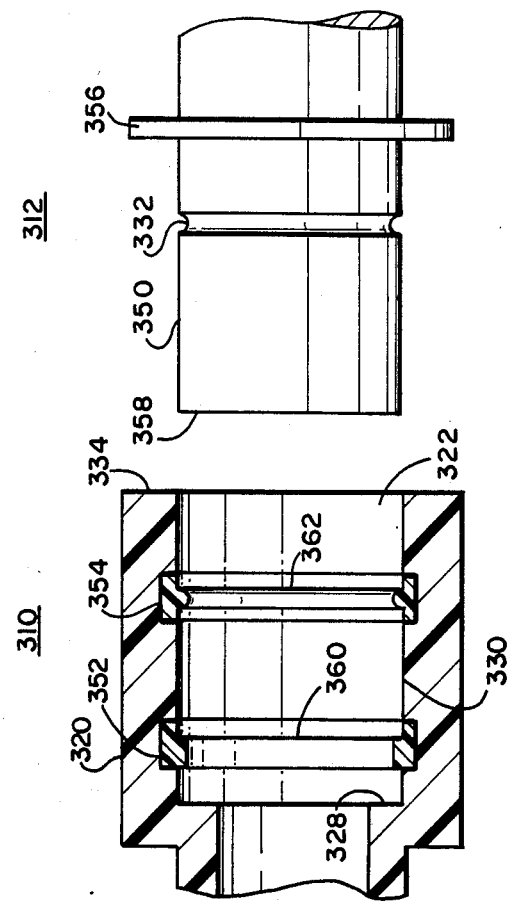
FIG. 3 is a longitudinal view of alternate embodiments of a portion of the male and female bodies of FIG. 1.

Referring now to FIG. 1, the male and female bodies designated generally 10 and 12 respectively are shown seperated but located along a common longitudinal axis. Female body 10 is shown in cross section and comprises a tubular shaped receiving end portion 20 which defines an interior region 22. Opposite from receiving end portion 20 and integrally connected therewith is a tube connecting portion 24 with a tapered saw tooth shaped outer surface. The tube connecting portion 24 is adapted to be inserted into a length of tube and the tapered saw tooth outer surface provides a gradually increasing frictional fit between the female body and the length of tube while preventing excessive distortion and deformation of the tubing. The entry portion of the length of tube is in fairly continuous contact with the saw tooth outer surface. The hollow interior 26 of the tube connecting portion 24 communicates with both the interior of the length of tube and the interior region 22.

In FIG. 1, the interior surface of the receiving end portion 20 is tapered, that is, the cross-sectional diameter of the interior region 22 at the open end of the receiving end portion 20 is larger than the parallel and spaced apart cross-sectional diameter of the interior region 22 defined at the rim 28 of the receiving end portion 20, and the wall 30 of the interior surface slopes linearly from the cross-sectional diameter at the open end to inner cross-sectional diameter at the rim 28. The interior surface of the receiving end portion 20 further comprises an annular groove 32.

Male body 12 comprises a tube connecting portion 40 similar in shape and purpose to the tube connecting portion 24 of the female body 10. However, it further comprises a pair of ledges only one of which 42 is shown which ledges project inwardly into the hollow interior 44 of the tube connecting portion 40. The ledges 42 are in the preferred embodiment located on a common diameter of the tube connecting portion 40.

Male body 12 further comprises a tubular shaped plug end portion 50 intergrally formed with the tube connecting portion 40 and adapted to be inserted into the interior region 22 of the receiving end portion 20. The interior of the plug end portion 50 communicates with the hollow interior 44 of the tube connecting portion 40 which in turn communicates with the interior of a length of tube when the tube connecting body 40 is inserted therein.

It should be appreciated that the term "tubular shaped" as used to describe the receiving end portion and the plug end portion includes hollow cylinders or bodies of various shaped cross sections including circular, rectangular and square cross sections.

The outer diameter (OD) of the generally cylindrically shaped plug end portion is uniform throughout its length except at grooves 52 and 54, shown in FIG. 2, and except for the annular ridge 56. The outer diameter of the plug end portion 50 is slightly less than the cross-sectional diameter of the interior region 22 at rim 28. For example, the outer diameter of the plug end portion in the preferred embodiment is approximately 0.359" while the cross-sectional diameter of the interior region 22 at the open end of the receiving end portion is approximately 0.398" and the cross-sectional diameter at rim 28 approximately 0.370".

The longitudinal length of the plug end portion from the open end 58 to the annular ridge 56 is substantially equal to the longitudinal length of the interior region 22 from the inner cross-sectional diameter at rim 28 to the outer edge of the receiving end portion 20. Annular ridge 56 contacts the outer surface 34 of the receiving end portion 20 as the open end 58 of the plug end portion 50 contacts the rim 28.

FIG. 2 is an enlarged cross section of a portion of the male body in FIG. 1 taken along the lines and arrows 2 in FIG. 1. The plug end portion 50 includes the annular rectangularly shaped grooves 52 and 54. In the preferred embodiment, the grooves are filled by inset molding with an elastomeric thermoplastic resin material which forms a pair of peripheral members 60 and 62. Ledges 42 assist in aligning the male body during the insert molding step. Inspection of FIGS. 1 and 2 show that the OD of both peripheral members 60 and 62 exceeds the OD of the plug end portion 50, with the peripheral member 62 having a slightly larger OD than the peripheral member 60. In the preferred embodiment, the OD of the peripheral member 60 is 0.383" and the OD of the peripheral member 62 is 0.391".

While the preferred material for the peripheral members 60 and 62 is an elastomeric thermoplastic resin, the preferred material for the male body is any rigid plastic material suitable for the intended application of the coupling. In medical applications a suitable rigid plastic material comprises a high density polyethylene or polypropylene.

An alternate method for forming the peripheral members 60 and 62 is as follows: the male body is formed by injection molding and, before the plastic material of which the male body is made sets, the peripheral members are formed by injection molding of an elastomeric thermoplastic resin. The plastic resin melt fills the male body mold in the grooves 52 and 54 and mixes with the plastic material of which the male body is composed at the mold interface surrounding the grooves 52 and 54. Here the primary melt of the male body intimately coalesces with the secondary melt of the thermoplastic resin to form a chemical and mechanical bond between the two materials. The injection molding step for both the male body and the peripheral members may take place simultaneously where an appropriate mold for the male body including the peripheral members is fabricated and both primary and secondary mold injection stations are established. Alternatively, the injection molding step of the male body occurs first followed soon after by the injection molding step for the peripheral members, the latter injection molding step occuring before the melt composition of the male body has set. A suitable method of performing the injection molding process described above is described further in U.S. Pat. No. 3,950,483.

Referring once again to FIG. 1, as the male body is inserted into the female body, the peripheral member 60 comes in contact with the wall 30 and is gradually compressed against the wall 30 as the male body is fully inserted. Deformation of the peripheral member 60 against the wall 30 forms a liquid seal. As the front edge 58 of the male body approaches the rim 28, the peripheral member 62 begins to seat itself within annular groove 32. The maximum dimension of groove 32 is approximately equal to the OD of the peripheral member 62. The curved shape of the peripheral member 62 aids in seating member 62 within annular groove 32. Positioning of member 62 in groove 32 acts to lock the female and male bodies together. Also, member 62 seated in groove 32 acts as a further liquid seal. The peripheral member 62 in combination with a tight fitting groove 32 acts as a liquid sealing and locking means.

Hence, bodies 10 and 12 are quickly connected together in one pushing action applied along their common longitudinal axis. All that is required to disconnect the bodies is a pulling force of each body away from the other again along their common longitudinal axis. A sufficient force must be applied to overcome the seating of peripheral member 62 in groove 32. Since member 62 is compressible, it will eventually give way and leave groove 32 as the pulling force increases. However, the locking force is sufficient that under normal use the connector will not separate. Since the peripheral members 60 and 62 are preferably an elastomeric material they return to their original shape after the bodies 10 and 12 are disconnected.

The tapered interior surface assists in bringing the male and female bodies into mating engagement. The frictional force encountered with deformation of member 60 as it slides along wall 30 also aids in locking the bodies together. Also, the tapered interior aids in seating peripheral member 62 into groove 32.

With the tube coupling of the present invention, there is no latch or locking mechanism requiring a separate action to disconnect the male and female bodies such as a squeeze or twisting action. The peripheral members which provide a seal also act to create a locking action. This is possible because the peripheral members 60 and 62 are a compressible material which is formed integral with the rigid material of the male member. In the case where the peripheral members are formed by injection molding before the male body melt composition has set, the chemical and mechanical bond formed thereby acts to avoid separation of the peripheral members 60 and 62 from the grooves 52 and 54 respectively.

FIG. 3 is an alternate embodiment 310 and 312 of a portion of the male and female bodies 10 and 12, respectively, of FIG. 1. The bodies 310 and 312 are equipped with tube connecting portions identical to tube connecting portions 24 and 40, respectively, and they accordingly are not shown in FIG. 3. Female body 310 comprises a receiving end portion 320 and a male body 312 comprises a plug end portion 350. However, instead of forming peripheral members in grooves on the external surface of the plug end portion 350, peripheral members 360 and 362 are formed within grooves in the interior surface of wall 330 of receiving end portion 320 by insert molding or simultaneous injection molding as described above. The cross-sectional diameter of the interior region 322 of the receiving end portion 320 is generally constant throughout its length from the interior rim 28 to the open end of the receiving end portion.

Spigot end portion 350 further comprises an annular groove 32 and an annular ridge 356. The cross-sectional diameter of the plug end portion 350 is generally constant throughout its length except for the annular groove 332. Also, the cross-sectional diameter of plug end portion 350 is generally less than then the cross-sectional area of the interior region 322. However, the inner diameter of both the peripheral members 360 and 362 are smaller than both the cross-sectional diameters of the interior region 322 and the plug end portion 350. As plug end portion 350 is inserted into the receiving end portion 320 the exterior surface of the plug end portion 350 frictionally contacts the peripheral members 360 and 362. The peripheral members 360 and 362 are made of a compressible material such as an elastomeric thermoplastic resin and as the plug end portion is inserted further into the interior region 322 they make a liquid seal with the exterior surface of the plug end portion 350. As the front end 358 of the plug end portion contacts the annular rim 328 the peripheral member 362 seats itself within the annular groove 332 of the plug end portion 350. At the same time annular ridge 356 engages the outer edge 334 of the receiving end portion 320.

The peripheral member 360 in the preferred embodiment has a rectangular cross section while the peripheral member 362 has a circular cross section. The circular cross section of peripheral member 362 aids in seating the peripheral member 362 and the annular groove 332.

The peripheral members 360 and 362 interacting with the plug end portion 350 act to create a liquid seal and, a positive locking action without interferring with a quick disconnect capability of the tube coupler.

While certain specific embodiments of the invention have been illustrated and described in detail herein, it is obvious that many modifications thereof may be made without departing from the spirit and scope of the invention.

What is claimed:

1. A quick disconnect coupling for connecting to two tube lengths to be coupled comprising:
    a male body having an elongated tubular shaped plug end portion;
    a female body having an elongated tubular shaped receiving end portion of substantially the same length as said plug end portion for receiving said plug end portion for mating engagement therewith; and
    at least a pair of spaced apart peripheral members made from a relatively compressible plastic material and molded within grooves in the tubular shaped portion of one of said bodies, a first one of said at least a pair of peripheral members disposed to be compressed against a surface of the tubular shaped portion of the remaining body and a second one of said at least a pair disposed to fit within a groove within the tubular shaped portion of said remaining body when said male and female bodies are matingly engaged, said first and second peripheral members cooperating together to form a liquid seal and locking engagement between said male and female bodies, the lengths of said elongated end portions and the spacing of said at least a pair of spaced apart peripheral members being such that said at least a pair of peripheral members act as a guide in preventing relative tilting of said male and female bodies with respect to their common longitudinal axis when coupled whereby said liquid seal is preserved.

2. The coupling of claim 1 wherein said male and female bodies comprise a relatively rigid synthetic plastic material and said at least a pair of peripheral members comprise an elastomeric thermoplastic resin material.

3. A quick-disconnect coupling for connecting to two tube lengths to be coupled comprising:
   a male body having an elongated tubular shaped plug end portion;
   a female body having an elongated tubular shaped receiving end portion for receiving said plug end portion therewithin in mating engagement; and
   at least a pair of spaced apart peripheral members made from a relatively compressible plastic material and molded within grooves surrounding said plug end portion, a first one of said at least a pair disposed to be compressed against the interior surface of said receiving end portion, and a second one of said at least a pair disposed to fit within a groove within said interior surface when said plug end portion matingly engages said receiving end portion, said first and second peripheral members cooperating together to form a liquid seal and locking engagement between said male and female bodies, the lengths of said elongated end portions and the spacing of said at least a pair of spaced apart peripheral members being such that said at least a pair of peripheral members act as a guide in preventing relative tilting of said male and female bodies with respect to their common longitudinal axis when coupled whereby said liquid seal is preserved.

4. The coupling of claim 3 wherein said receiving end portion comprises a tapered interior surface, said first one of said at least a pair of peripheral members having an outside diameter less than said second one and disposed on said plug end portion to engage said tapered interior surface before said second peripheral member as said male and female bodies are engaged.

5. The coupling of claim 4 wherein said male and female bodies comprise relatively rigid synthetic plastic material and said at least a pair of peripheral members comprise an elastomeric thermoplastic resin material.

* * * * *